(12) United States Patent
Goncalves

(10) Patent No.: US 8,431,077 B2
(45) Date of Patent: Apr. 30, 2013

(54) HYDROGEN PEROXIDE STERILIZATION PROCESS AND DEVICE

(76) Inventor: Helder da Costa Goncalves, Boticas (PT)

( * ) Notice: Subject to any disclaimer, the term of this patent is extended or adjusted under 35 U.S.C. 154(b) by 345 days.

(21) Appl. No.: 12/668,256

(22) PCT Filed: Jul. 10, 2007

(86) PCT No.: PCT/PT2007/000029
§ 371 (c)(1),
(2), (4) Date: Jan. 8, 2010

(87) PCT Pub. No.: WO03/072150
PCT Pub. Date: Sep. 4, 2003

(65) Prior Publication Data
US 2010/0272603 A1    Oct. 28, 2010

(51) Int. Cl.
*A61L 2/16* (2006.01)
(52) U.S. Cl.
USPC ....... 422/34; 422/28; 422/32; 436/1; 436/135
(58) Field of Classification Search ............... 422/28, 422/32, 34; 436/1, 135
See application file for complete search history.

(56) References Cited

U.S. PATENT DOCUMENTS

| | | | |
|---|---|---|---|
| 5,173,258 A * | 12/1992 | Childers | 422/27 |
| 6,451,254 B1 | 9/2002 | Wang et al. | |
| 2004/0109799 A1 | 6/2004 | Kadlec et al. | |
| 2005/0147527 A1 | 7/2005 | Brown et al. | |

FOREIGN PATENT DOCUMENTS

| | | |
|---|---|---|
| CA | 2519664 | 3/2007 |
| DE | 3636716 | 5/1988 |
| EP | 1764115 | 9/2005 |
| EP | 1884250 | 6/2008 |
| WO | 9704816 | 2/1997 |
| WO | 2004041316 | 5/2004 |

* cited by examiner

*Primary Examiner* — Lyle Alexander
(74) *Attorney, Agent, or Firm* — Cowan, Liebowitz & Latman, P.C.; Mark Montague, Esq.

(57) ABSTRACT

This invention concerns a hydrogen peroxide sterilization device, with injection of hydrogen peroxide vapor, provided with a vaporizer that feeds a sterilization chamber, with a dose that varies in function of the control performed by a computer or control unit. The vaporizer works with a pressure inferior to the atmospheric one and is heated by an electrical resistance heater, or by micro-waves. All the vaporization process is made in vacuum, by heat or ultra-sounds. The filling of the sterilant agent is made drop-by-drop by a capillary tube which transforms the liquid into a pulverized gas. The computer controls the electrical valve following the dosing pump from the pressure and/or temperature information that comes from various pressure and/or temperature sensors, whereby the pressure inside the chamber is maintained during the sterilization process in a constant predefined value, appropriate to use simple cellulose-base paper or paper composed to the packaging of the devices. The invention also refers to the hydrogen peroxide sterilization process that uses the referred device. The present invention is also appropriate to sterilize cork stoppers and stomatology material in chambers of reduced size, or other suitable materials for sterilization in bigger chambers. Based on the invention it is possible to create the REGISTOMETER FOR EVALUATING BIOLOGICAL INDICATORS AND CHEMICAL INDICATORS for laboratory studies of biological death and color change of chemical indicators, with hydrogen peroxide as sterilization agent.

4 Claims, 2 Drawing Sheets

CYCLE TYPE CURVES

HYDROGEN PEROXIDE STERILIZATION PROCESS AND DEVICE

The invention refers to a process and device for the hydrogen peroxide sterilization and it is based on the hydrogen peroxide vapour injection into a sterilization chamber with a temperature between 20° C. and 70° C. The process takes place in a chamber with two doors (with sanitary barrier) warmed between 20° C. and 70° C.

PREVIOUS INVENTIONS

Document WO 03072150 discloses a vapour generation unit which receives an aqueous hydrogen peroxide solution and includes a desiccant cartridge product.

Document EP1764115 describes a sterilization system which includes a hydrogen peroxide generator. It has a space for the introduction of the hydrogen peroxide in a treatment space and dehumidifier. It is important to note that there is a dehumidified air passage between the dehumidifier and the treatment space.

Document CA2519664 describes a sterilization process where the hydrogen peroxide solution is dripped from an injector into an evaporator during 3 minutes with a flow of 5 g/minute. The working chamber is filled with hydrogen peroxide after the reduction of the inside humidity from 1 to 10%. The sterilization occurs thanks to the hydrogen peroxide saturation inside the working chamber.

It is necessary to mention the technical documents in EP 06398011 application filed by the present applicant referring to a hydrogen peroxide sterilization device. According to that patent application, the extracted hydrogen peroxide from the chamber is burned thanks to a high tension inside a plasma generator, which plasma generator may be part of the chamber.

The present patent application results from an improvement and development of the invention described in patent application EP 06398011.

ADVANTAGES OF THE DEVICE OF THE PRESENT INVENTION

- The drop-by-drop vaporization device has advantages compared to the existing ones, as the precision obtained with the sterilant agent dripping, using a capillary tube in the vaporizer and the doses variability applied through a computerized control system, which monitors the functioning of the device through various pressure and temperature probes. The dosing system is not made by only one dose system as it happens in other sterilizers.
- The vaporizer vaporizes 1-6 ml of hydrogen peroxide for a period of 3-100 seconds. It does not work necessarily in the saturation.
- Concerning the injection, the injection device does not have a syringe injector but a capillary tube inside the vaporizer, which transforms the liquid into pulverized gas. Heat or ultra-sounds can be used for the vaporization.
- The invention sterilization process occurs after the pressure within the vaporizer reaches less than 1 mbar and all the sterilization process is performed in vacuum;
- The invention vaporizer is physically opened to the chamber, and there is no valve between the vaporizer and the chamber;
- In the invention device, the vaporizer is part of the chamber;
- The control system is not based on the relative humidity, but it is based on the chamber pressure and in the number of apertures of the vaporizer valve, interacting with the temperature inside the chamber.

DRAWINGS DESCRIPTION

The invention is now described as a non limitative example with reference to the attached drawings.

DETAILED DESCRIPTION

Figure 1:
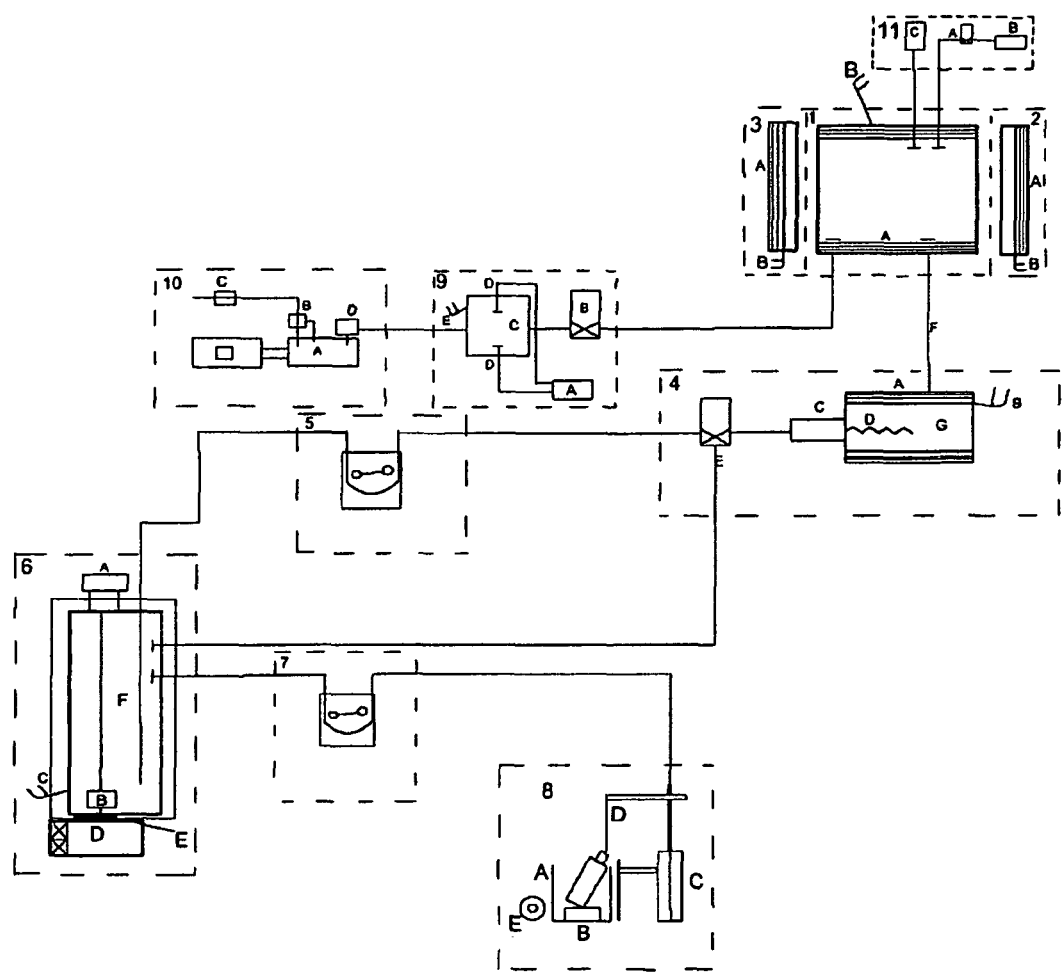
FIG. 1 shows a device scheme drawing which allows accomplishing the sterilization process according to the invention.
Figure 2:
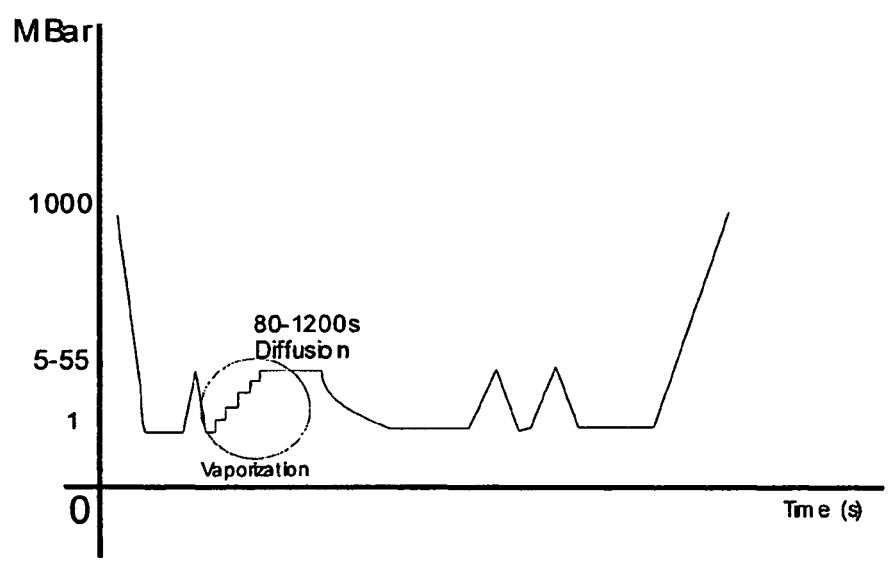
FIG. 2 is a graphic depicting the device functioning with the pressure evolution in the vaporizer depending on the time.

Referring to FIG. 1, the perforating unit (8) is composed by a drawer (8A), a recognition container sensor RFID, TAG, microchip (8B), a perforating cylinder (8C) and a closing drawer cylinder (8E). The drawer where the sterilant agent recharge is placed works with an electric and/or pneumatic cylinder mechanism, after recognizing the recharge through RFID, TAG or microchip identification. After recognizing the recharge, the automation system prints the recharge data in the system printer.

The sensor (8B) reads and accepts the sterilant agent recharge, and the recharge is used according to the manufacturer instructions.

After the recharge has been recognized, the drawer (8A) is closed and the needle (8D) perforates the recharge. This needle works thanks to a mechanical and/or electrical system. After the perforation, the sterilant agent is pumped by the pump (7) and placed into the tank (6F), which has the temperature controlled between −10° and 22° C., by an assembly of ventilator and peltier plate.

The sterilant agent is removed from the tank (6F); thanks to a dosing pump (5) the liquid passes through a vaporization valve (4E) which introduces the hydrogen peroxide into the vaporizer capillary tube (4D). The sterilant agent tank (6F) is provided with a system that controls the float (6B) and interacts with the computer or the control unit, in order to prevent the cycles to initiate without the sterilant agent in the tank of the sterilant agent. The level of sterilant agent is controlled by the level sensor (6A).

The sterilant agent vaporization is dripped and is obtained by a new device which includes vaporizer (4G), within which there is a capillary tube (4D) heated by an electrical resistance heater (4A), is fed by a dosing pump (5).

As the vaporization is dripped, it is possible to dosing small vapour quantities from the vaporizer chamber (4G) to the sterilization chamber (1A).

With said vaporization method it is possible to sterilize material packed in cellulose-based common paper, per se or made of synthetic fibers, besides the Tyvek® or polypropylene-based packaging products.

The process is developed inside a sterilization chamber (1A) with two doors (with sanitary barrier) heated between 20° C. and 70° C. in order to achieve a biological kill inside a "PCD" with 10 meters length.

This vaporizer (4) is essentially based on a chamber (4G)—provided with an electrical resistance heater (4A)—needs to have a programming command, in order to control the opening/closing of the vaporizer valve (4E), after the continuous pressure calculation. Between the product entry valve (4E) and the vaporizer (4G) there is a device designed for the drop-by-drop vaporization. The dosing is ensured by an electrical valve (4E) at the entry of the vaporizer, commanded by a computer or control unit.

After being heated by the vaporizer (4G) the capillary tube (4D) is able to vaporize drop-by-drop with a programmed command by the computer.

The vaporizer (4G) is heated by an electrical resistance heater (4A), or by a micro-wave system, at a temperature between 30° C. and 200° C. Ultra-sounds can also be used for the vaporization. The vaporizer (4A) has a pressure and/or temperature probe (4B) which sends the information to the control computer. The hydrogen peroxide is injected drop-by-drop into the vaporizer (4G), which is mechanically connected to the sterilization chamber (1A) by a clamp system with a Teflon tube (4F) which conveys the hydrogen peroxide and allows the entry of the vapour inside the chamber (1A) in the best conditions.

Between the dosing pump (5) and the vaporizer valve (4E) there is a return line of the sterilant agent to remove the air from the tubing of the injection circuit of the sterilant agent.

Near the vaporizer entry valve (4E), there is an air removing system thanks to a vacuum pump (10A), which removes the air before starting the drop-by-drop injection. The gas passes through a plasma generator (9C) with high-tension electrodes (9D), which catalyzes the hydrogen peroxide at the chamber exit, breaking the hydrogen peroxide in water, oxygen and free radicals by a plasma effect, and can be or not an integral part of the chamber.

The sterilization chamber (1A) has a pressure and/or temperature probe (11C e 1B) which informs the computer that controls the process.

According to the drawing 1, in order to achieve a drop-by-drop injection, the capillary tube (4D) has a length between 50 mm and 2500 mm with a hole from 1 μmm to 0.1 mm, which allows the drop-by-drop vaporization. The entry valve (4E) is controlled based in the value vaporized in each opening. There will be successive openings of the valve until reaching the established value for a pressure between 5 mbar and 655 mbar.

The dosing system has no air, which means that if there is less material inside the chamber for the same value of pressure, it will be necessary to inject less hydrogen peroxide. On the other hand, if there is more material inside the chamber for the same pressure value, it will be necessary to inject more hydrogen peroxide. This occurs due to the possible condensation of the sterilant agent inside the chamber.

The sterilization is reached in lumen with 10 meters of length and 1 mm diameter with biological indicators Stearothermophilus inside a container inserted inside the lumen in a population of $1.2 \times 10^6$ during the sterilization period between 80 and 2200 seconds (diffusion phase).

The dripping dosing system is ensured by a peristaltic pump (5)—or other—between the tank of the sterilant agent and the vaporizer that starts the pumping with 1 to 800 periods before the injection, in order to remove all the air in the tubes. After this pumping period, and air removal from the tubes, the vaporizer valves (4E) open with intermittent opening controlled by the pressure read in the sterilization chamber (1A).

With this process, there is a curve of vaporization with an entry similar with that shown on the drawing 2. The diffusion period occurs between 80 and 2200 seconds with a pressure between 5 and 655 mbar and may have an addition of air in the chamber.

Modifications can be made to the disclosed sterilization device, maintaining the functioning principle in the attached claims, for example modifications with equivalent element, which fall in the scope of this invention.

The device of the present invention is also appropriate to the sterilization of stomatology material in a reduced size chamber, cork stoppers commonly used in wine bottles, endoscopes and videoscopes among others.

This device also presents Penetration Test cycle of the sterilant agent and a cycle of Leak Test, which can be independent or simultaneous.

This device also performs functions of a RESISTOMETER FOR EVALUATING BIOLOGICAL INDICATORS for laboratory studies of biological death using hydrogen peroxide as sterilization agent.

The invention claimed is:

1. A Hydrogen peroxide sterilization device with hydrogen peroxide vapor injection comprising:
   a tank (6F);
   a sterilization chamber (1A);
   a dosing pump (5);
   an electrical valve (4E);
   a vaporizer (4G), comprising a capillary tube (4D);
   an electrical resistance heater (4A);
   various pressure and/or temperature sensors;
   a computer or control unit programmed to control a dose fed to said sterilization chamber (1A) by controlling the electrical valve (4E) following the dosing pump (5) taking into account information concerning the pressure and/or temperature coming from said various pressure and/or temperature sensors, and wherein the pressure inside the chamber is maintained during the sterilization process at a constant predefined value;
   wherein the dosing pump (5) removes the sterilant agent from the tank (6F) passing it through the vaporization valve (4E) and introducing it into the capillary tube (4D),
   wherein the vaporizer (4G) feeds the sterilization chamber (1A) and to work with a sub-atmospheric pressure;
   wherein the electrical resistance heater heats the vaporizer (4G);
   wherein the capillary tube (4D) fills the sterilant agent drop-by-drop and to transform the liquid into a pulverized gas.

2. The Hydrogen Peroxide Sterilization and/or Disinfection Process, characterized by using the device according to claim 1.

3. The device according to claim 1, wherein the capillary tube (4D) has a length between 50 mm and 2500 mm.

4. The device according to claim 1, wherein the capillary tube (4D) has a hole between 1 μmm to 0.1 mm.

* * * * *